United States Patent [19]

Camaggi et al.

[11] Patent Number: 5,470,863
[45] Date of Patent: Nov. 28, 1995

[54] OXIMIC DERIVATIVES WITH A FUNGICIDE ACTIVITY

[75] Inventors: Giovanni Camaggi, Novara; Lucio Filippini, San Donato Milanese; Marilena Gusmeroli, Monza; Giovanni Meazza, Saronno; Giampaolo Zanardi, Vigevano; Carlo Garavaglia, Cuggiono; Luigi Mirenna, Milan, all of Italy

[73] Assignee: Ministero Dell'Universita' E Della Ricerca Scientifica E Technologica, Rome, Italy

[21] Appl. No.: 943,333

[22] Filed: Sep. 10, 1992

[30] Foreign Application Priority Data

Sep. 13, 1991 [IT] Italy ................ MI91A2422

[51] Int. Cl.⁶ ............... A01N 43/36; A01N 43/40; C07D 207/335; C07D 401/12
[52] U.S. Cl. ............. 514/343; 514/367; 514/427; 546/281; 548/170; 548/253; 548/255; 548/267.4; 548/314.7; 548/561
[58] Field of Search .................. 548/561, 170; 546/281; 514/343, 395, 427, 367

[56] References Cited

U.S. PATENT DOCUMENTS

| | | | |
|---|---|---|---|
| 4,883,807 | 11/1989 | Clough et al. | 548/561 |
| 5,055,471 | 10/1991 | de Fraine et al. | 514/427 |
| 5,091,407 | 2/1992 | de Fraine et al. | 548/333.5 |

FOREIGN PATENT DOCUMENTS 0273572 6/1988 European Pat. Off. .

OTHER PUBLICATIONS

Methoden Der Organischen Chemie, Eugen Muller, Georg Thieme Verlag, 1971; pp. 1181–1198.
The Chemistry of Heterocyclic Compounds, Triazoles 1,2,3, John Montgomery, John Wiley and Sons, 1980; p. XI.
The Chemistry of Heterocyclic Compounds, Pyrroles Part One, The Systhesis and The Physical and Chemical Aspects Of The Pyrrole Ring, R. Alan Jones, John Wiley and Sons, 1990; pp. 105–107.
The Chemistry Of Heterocyclic Compounds, Triazoles 1,2, 4, Carrol Temple Jr., John Wiley and Sons, 1981; pp. XI–XIV.
Comprehensive Heterocyclic Chemistry: The Structure, Reactions, Synthesis and Uses of Heterocyclic Compounds, vol. 5, Kevin T. Potts, 1986; pp. 373–374.
D. Moderhack, Chemische Berichte Jahrg, vol. 108, 1975; pp. 887–896.
D. Moderhack, Chem. Abst. vol. 88, 1978; p. 37713, No. 37706C.

*Primary Examiner*—R. W. Ramsuer
*Attorney, Agent, or Firm*—Rogers & Wells

[57] ABSTRACT

A description follows of oximic derivatives with a fungicide activity, for agricultural use, having the formula (I):

$$
\begin{array}{c}
A \!-\!\!-\!\! B \quad N\!-\!O\!-\!W\!-\!L\!-\!Y \\
\parallel \quad \parallel \\
D \diagdown_{N} \diagup^{C} \diagdown_{R_3} \\
\mid \\
R_2O\!-\!CH\!=\!C\!-\!COOR_1
\end{array}
\qquad (I)
$$

wherein:
A, B, D, are N, or =C—G;
G is H, halogen, $NO_2$, CN, —$COOR_4$, $C_1$–$C_6$ (halo)alkyl
$R_1$, $R_2$, $R_4$ and $R_5$, are $C_1$–$C_6$ (halo)alkyl;
$R_3$ is H, $C_1$–$C_6$ (halo)alkyl or —$COOR_5$;
W is $C_2$–$C_{10}$ alkylene;
L represents O or S;
Y represents phenyl, naphthyl, heterocycle, substituted alkyl.

12 Claims, No Drawings

OXIMIC DERIVATIVES WITH A FUNGICIDE ACTIVITY

The present invention relates to oximic derivatives having a high fungicide activity, the process for their preparation and their use in agriculture.

European Patent 273572 discloses oximic derivatives with a fungicide activity including compounds having the general formula:

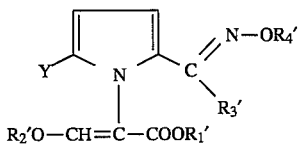

wherein:
- $R_1'$, $R_2'$ are alkyls, Y can be hydrogen, halogen, nitro group, cyano group, alkyl optionally substituted;
- $R_3'$ can be COOalkyl optionally substituted, hydrogen, alkyl optionally substituted;
- $R_4'$ can be among other things hydrogen, alkyl, cycloalkyl, cycloalkylalkyl, all optionally substituted.

We have found a group of oximic compounds which differ from those of the known art and which have a higher fungicide activity.

The present invention therefore relates to oximic derivatives, with a fungicide activity, having the general formula (I)

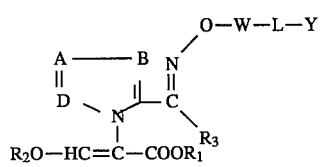

wherein:
- A, B, D, the same or different, represent a nitrogen atom, or a =C—G group;
- G represents a hydrogen atom, a halogen atom, the nitro group, the cyano group, a —COOR$_4$ group, a $C_1$-$C_6$ alkyl group or $C_1$-$C_6$ haloalkyl group;
- $R_1$, $R_2$, $R_4$ and $R_5$, the same or different, represent $C_1$-$C_6$ alkyl or $C_1$-$C_6$ haloalkyl groups;
- $R_3$ represents a hydrogen atom, a $C_1$-$C_6$ alkyl or $C_1$-$C_6$ haloalkyl group, or a —COOR$_5$ group;
- W represents a linear or branched $C_2$-$C_{10}$ alkylene, possibly substituted with one or more halogen atoms, or a $C_3$-$C_6$ cycloalkyl, a $C_4$-$C_8$ cycloalkylalkyl;
- L represents O or S;
- Y represents a phenyl, a naphthyl, heterocycle with 5–6 atoms wherein the heteroatoms are O, N, S, a benzocondensated heterocycle with 9–10 atoms wherein the heteroatoms are selected from oxygen, nitrogen, sulphur, all said groups being optionally substituted with one or more groups selected from: halogen atoms, $C_1$-$C_4$ alkyls or $C_1$-$C_4$ haloalkyls, $C_1$-$C_4$ alkoxyls or $C_1$-$C_4$ haloalkoxyls, phenyl groups or phenoxy groups suitably substituted;
- Y can also be a linear or branched alkyl, substituted with at least one or more groups selected from: halogen atoms, $C_1$-$C_4$ alkoxyls or $C_1$-$C_4$ haloalkoxyls or $C_1$-$C_4$ haloalkoxyhaloalkoxyl, phenyl groups or phenoxylic groups suitably substituted.

The structure of the general formula (I) may represent at least two types of E/Z isomerisms.

The compounds having general formula (I) can be prepared with different processes, some of which are described hereafter as examples.

A general method for obtaining the compounds having formula (I), consists in the condensation of a carbonylic compound having formula (II):

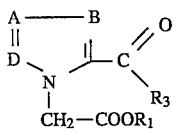

with a hydroxylamine having formula (III):

$$NH_2-O-W-L-Y \quad (III)$$

free or salified, possibly in the presence of an organic or inorganic base, in a dipolar protic or aprotic solvent, at a temperature ranging from 0° to 80° C., followed by the reaction of the compound having formula (IV) thus obtained

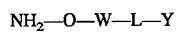

with an alkyl formiate having formula (V):

$$H-CO-OR_6 \quad (V)$$

where $R_6$ represents a $C_1$-$C_3$ alkyl, in a dipolar protic or aprotic solvent, or in excess of the alkyl formiate, in the presence of an organic or inorganic base, at a temperature ranging from −10° C. to 80° C., to obtain the corresponding salt of the compound having formula (VI):

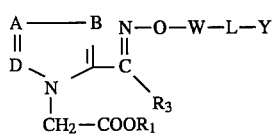

which in the same reaction environment, in the presence of an $R_2$—X alkylating agent, where X represents a halogen atom (Cl, Br, I) or an activated ester, such as p-toluensulphonate, at a temperature ranging from −10° C. to 80° C., is transformed into the desired compound having formula (I).

The compounds having formula (II) can be prepared by reaction of (VII):

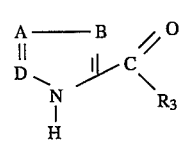

with an ester (VIII):

$$R_1-O-CO-CH_2-X \quad (VIII)$$

The hydroxylamines having formula (III) can be prepared according to the known methods of the art, described for example in HOUBEN WEYL "METHODEN DER ORGANISHEN CHEMIE", Vol X/1 1181 (1971).

The compounds having general formula (VII) can be obtained by different processes, depending on the nature of A, B and D.

When A, B and D, represent a =C—G group, the compounds having formula (VII) can be prepared according to the methods for the synthesis of pyrroles mentioned for example in "THE CHEMISTRY OF HETEROCYCLIC COMPOUNDS" vol. 48, part 1, R. A. JONES (Ed.), WILEY, 1990.

When A and D are both =N— and B represents a =C—G group, the compounds having formula (VII) can be prepared according to the methods for the synthesis of 1,2,3-triazoles mentioned for example in "THE CHEMISTRY OF HETEROCYCLIC COMPOUNDS" Vol. 39, J. A. MONTGOMERY (Ed), WILEY, 1980.

When A and B are both =N— and D represents a =C—G group, the compounds having formula (VII) can be prepared according to the methods for the synthesis of 1,2,4-triazoles mentioned for example in "THE CHEMISTRY OF HETEROCYCLIC COMPOUNDS", Vol 37, J. A. MONTGOMERY (Ed.), WILEY, 1981.

When A and D both represent =C—G groups and B is =N— the compounds having formula (VII) can be prepared according to the methods for the synthesis of imidazoles mentioned for example in "COMPREHENSIVE HETEROCYCLIC CHEMISTRY", Vol. 5, page 373, K. T. POTTS (Ed.), PERGAMON, 1984.

When A, B and D are =N—, the compounds having formula (VII) can be prepared according to the methods for the synthesis of tetrazoles: D. MODERHACK, CHEMBER. 1975, 108, 887; D. MODERHACK, CHEM. ZTG., 1977, 101, 403 (C.A.1978, 88, 37706).

The compounds having general formula (I) have a particularly high fungicide activity against phytopathogen fungi which attack cultivations of vines, cereals, Cocurbitacee and fruit trees.

Plant diseases which can be fought with the compounds of the present invention are, for example, the following:

Helminthosporium of cereals

*Plasmopara viticola* of vines phytium of vegetables

*Sphaerotheca fuliginea* of cucurbitacee (e.g. cucumbers)

Septoria of cereals

*Erysiphe graminis* of cereals

Rynchosporium of cereals

*Podosphaera leucotricha* of apple trees

*Uncinula necator* of vines

*Venturia inequalis* of apple trees

*Piricularia Oryzae* of rice

Botrytis cinerea

Fusarium of cereals

The compounds having formula (I) are capable of carrying out a fungicide action which is both curative and preventive and have little or no phytotoxicity.

For practical use in agriculture it is often useful to have fungicidal compositions containing one or more compounds corresponding to formula (I), possibly also in isomeric form, as an active substance.

These compositions can be applied on any part of the plant, for example on the leaves, stems, branches and roots, or on the seeds, before seeding, or even on the soil where the plant grows.

Compositions can be used in the form of dry powders, wettable powders, emulsionable concentrates, micro-emulsions, pastes, granulates, solutions, suspensions etc.: the choice of the type of composition depends on the specific use.

The compositions are prepared with the known methods, for example by diluting or dissolving the active substance with a solvent and/or solid diluent, possibly in the presence of surface-active agents.

Solid diluents or supports which can be used are: silica, kaolin, bentonite, talc, infusorial earth, dolomite, calcium carbonate, magnesia, chalk, clays, synthetic silicates, attapulgite, sepiolite.

As liquid diluents, it is possible to use, apart from water naturally, various types of solvents, for example aromatics (xylenes or mixtures of alkylbenzoles), chloro aromatics (chlorobenzole), paraffins (fractions of petroleum), alcohols (methanol, propanol, butanol, octanol,) amines, amides (N,N'-dimethylformamide, N-methylpyrrolidone), ketones (cyclohexanone, acetophenone, isophorone, ethylamylketone), esters (isobutyl acetate).

As surface-active agents: salts of sodium, calcium or triethanolamine of alkylsulphates, alkylsulphonates, alkylarylsulphonates; polyethoxylated alkylphenols, fat alcohols condensed with ethylene oxide, polyoxyethylated fatty acids, polyoxyethylated esters of sorbitol, ligninsulphonates.

The compositions may also contain special additives for particular purposes, for example adhesion agents such as arabic rubber, polyvinylic alcohol, polyvinylpyrrolidone.

If desired it is possible to also add to the compositions of the present invention other compatible active substances, such as fungicides, phytoregulators, antibiotics, weed-killers, insecticides, fertilizers.

The concentration of active substance in the above compositions can vary within a wide range, depending on the active compound, the cultivation, pathogen, environmental conditions and the type of formulation used.

In general the concentration of active substance varies from 0.1 to 95%, preferably from 0.5 to 90%.

The following examples illustrate the invention.

EXAMPLE 1

Preparation of (Z)-3-methoxy-2-{2-[2-(3-trifluoromethylphenoxy)ethoxyiminomethyl]pyrrol-1-yl}methyl prop-2-enoate (compound No.1).

0.60 g of 60% (p/p) sodium hydride in vaseline are dispersed in 15 cm$^3$ of anhydrous DMF under a nitrogen atmosphere.

2.8 g of 2-{2-[2-(3-trifluoromethylphenoxy) ethoxyiminomethyl]pyrrol-1-yl}methyl acetate in 4.7 cm$^3$ of ethyl formiate are then added to the solution dropwise.

The mixture thus obtained is stirred at room temperature for 2 h.

It is cooled to 10° C. and 4.7 cm$^3$ of CH$_3$I are added.

The mixture is kept for 2.5 h at room temperature, and is then poured into a saturated solution of NH$_4$Cl and extracted with ethyl acetate.

The organic phase is washed with brine, anhydrified on sodium sulphate and concentrated at reduced pressure.

The crude product obtained (3.9 g) is purified by silica gel chromatography, eluating with a mixture of petroleum ether/ethyl acetate=9/1.

1.9 g of compound No.1 are obtained, whose structure is shown in Table 1 and NMR spectroscopic data in Table 2.

EXAMPLES 2–13

Using the same procedure described in Example 1 compounds 2–13 were prepared, their structure being shown in Table 1 and respective NMR spectroscopic data in Table 2.

EXAMPLE 14

Preparation of 2-{2-[2-(3-trifluoromethylphenoxy) ethoxyiminomethyl]pyrrol-1-yl}-methyl acetate.

A suspension of 2.6 g of (2-carboxyaldehydepyrrol-1-yl)methyl acetate, 4 g of o-[2-(3-trifluorophenoxy)ethyl]-hydroxylamine hydrochloride and 1.3 g of sodium acetate in 25 cm$^3$ of ethanol is stirred vigorously for 2 h at room temperature.

It is diluted with 200 cm$^3$ of water, and extracted with $CH_2Cl_2$, the organic extracts are washed with a saturated solution of $NaHCO_3$ and then with water, to be subsequently anhydrified with $Na_2SO_4$ and concentrated under vacuum.

The crude product obtained is purified by silica gel chromatography, eluating with the mixture petroleum ether/ethyl acetate=9/1.

2.9 g of the desired compound are obtained.

EXAMPLE 15

Preparation of o-[2-(3-trifluorophenoxy)ethyl]hydroxylamine hydrochloride.

The following products are added to anhydrous DMF under a nitrogen atmosphere: 3-trifluoromethylphenol (10 cm$^3$), 1,2-dibromoethane (15 cm$^3$) and potassium carbonate (11 g).

The mixture is heated for 16 h to 70°–80° C.

It is diluted with water and the reaction is basified (pH=14) by adding NaOH, and is then extracted with ethyl acetate.

The organic phase is anhydrified on sodium sulphate and concentrated at reduced pressure.

The crude product obtained is purified by silica gel chromatography, eluating with hexane/ethyl acetate=9:1.

9 g of 1-bromo-2-(3-trifluoromethylphenoxy)ethane are obtained, which is reacted with N-hydroxyphthalimide (4.4 g) and (3.8 cm$^3$) of triethylamine in 40 cm$^3$ of DMF for 10 h, in a nitrogen atmosphere and at a temperature of 50° C.

The mixture is then diluted with water, acidified with 10% hydrochloric acid and extracted with ethyl acetate.

The organic extracts are concentrated at reduced pressure and the crude product (7.9 g) is recovered with 1.15 cm$^3$ of ethanolamine in 35 cm$^3$ of ethyl acetate.

The solution is heated for 2 h to 60° C., and is then diluted with 60 cm$^3$ of water and 60 cm$^3$ of ethyl acetate.

The organic phase is washed with water until neutral, dried on $Na_2SO_4$ and treated at room temperature with gaseous HCl.

The precipitate is filtered to obtain 4 g of the desired compound.

EXAMPLE 16

Determination of the preventive fungicide activity against cucumber mildew (*Sphaerotheca fuliginea* "Schlech" Salmon).

Cucumber plants cv. Marketer, grown in a vase in a conditioned environment, were sprayed on the lower faces of the leaves with the products under examination in a 20% hydroacetonic solution in acetone (w/w).

The plants were then kept in a conditioned environment for 1 day and subsequently sprayed on the upper face of the leaves with an aqueous suspension of conidia of *Sphaerotheca fuliginea* (200000 conidia per cm$^3$).

The plants were then brought back to a conditioned environment at 20° C. and 70% relative humidity.

At the end of the incubation period of the fungus (8 days), the gravity of the infection was evaluated with indexes of an evaluation scale from 100 (=healthy plant) to 0 (=completely infected plant).

Using compounds 2 and 5 in a concentration of 125 ppm an index=100 was obtained.

EXAMPLE 17

Determination of the preventive fungicide activity against *Helminthosporium teres*.

Barley leaves cv. Arna, grown in a vase in a conditioned environment, were sprayed on both faces with the products under examination in a 20% hydroacetonic solution in acetone (w/w).

After remaining 2 days in a conditioned environment at 20° C. and 70% relative humidity, the plants were sprayed on both faces of the leaves with an aqueous suspension of conidia of *Helminthosporium teres* (250000 conidia per cm$^3$).

After remaining 24 h in an environment saturated with humidity, at 21° C., the plants were kept in a conditioned environment for the incubation of the fungus.

At the end of this period (12 days), the gravity of the infection was evaluated with indexes of an evaluation scale from 100 (=healthy plant) to 0 (=completely infected plant).

Using compound No.5 in a concentration of 125 ppm an index=100 was obtained.

EXAMPLE 18

Determination of the curative fungicide activity against vine mildew (*Plasmopara viticola*) (B.et C.) (Berl et de Toni).

Vine leaves cv. Dolcetto, grown in a vase in a conditioned environment, at 25° C. and 60% relative humidity, were sprayed on the lower face with an aqueous suspension of conidia of *Plasmopara viticola* (200000 conidia per cm$^3$).

After remaining 24 h in an environment saturated with humidity at 21° C., the plants were sprayed on both faces of the leaves with the products under examination in a 20% hydroacetonic solution of acetone (w/w).

At the end of the incubation period of the fungus (7 days), the gravity of the infection was evaluated with indexes of an evaluation scale from 100 (=healthy plant) to 0 (=completely infected plant).

Using compound No.1 in a concentration of 125 ppm an index=100 was obtained.

EXAMPLE 19

Determination of the preventive fungicide activity against vine mildew (*Plasmopara viticola*) (B.et C.) (Berl et de Toni).

Vine leaves cv. Dolcetto, grown in a vase in a conditioned environment, at 25° C. and 60% relative humidity, were sprayed on both faces of the leaves with the products under examination in a 20% hydroacetonic solution in acetone (w/w).

After remaining 1 day in a conditioned environment at 20° C. and 60% relative humidity, the plants were sprayed on both faces of conidia of *Plasmopara viticola* (200000 conidia per cm³).

At the end of the incubation period of the fungus (7 days), the gravity of the infection was evaluated with indexes of an evaluation scale from 100 (=healthy plant) to 0 (=completely infected plant).

Using compounds No.1, 2, 4, 5 in a concentration of 30 ppm a control of over 90% was obtained.

EXAMPLE 20

Table 3 indicates the data concerning the preventive fungicide activity against vine mildew, according to the procedure of Example 14, and against Helminthosporium teres, according to the procedure of Example 12, of compounds No.1,2,4,5 described in the present invention compared with similar compounds described in European Patent 273572, whose structural formulae are shown in Table 1, and indicated as Ref.1,3,5,9.

TABLE 2-continued

| Compound | NMR 200 MHz (CDCCl₃) spectroscopic data |
|---|---|
| 10 | 7.96(1H, s), 7.71(1H, s), 7.48(7H, m), 6.67(1H, t), 6.58(1H, q), 6.29(1H, t), 4.45(2H, t), 4.34(2H, t), 3.76(3H, s), 3.69(3H, s). |
| 11 | 7.90(1H, s), 7.49(1H, s), 6.95(11H, m), 6.27(1H, q), 4.34(2H, t), 3.81(3H, s), 3.67(3H, s). |
| 12 | 7.87(1H, s), 7.63(1H, s), 7.53(1H, s), 7.43(1H, q), 6.69(1H, m), 6.57(2H, m), 6.29(1H, q), 4.25(4H, s), 3.87(3H, s), 3.71(3H, s). |
| 13 | 7.90(1H, s), 7.52(1H, s), 7.25(2H, s), 6.60(2H, m), 6.25(1H, m), 4.30(4H, m), 3.90(3H, s), 3.70(3H, s). |

TABLE I

| Compound | A | B | D | R1 | R2 | R3 | W | L | Y |
|---|---|---|---|---|---|---|---|---|---|
| 1 | H—C | H—C | H—C | CH₃ | CH₃ | H | —(CH₂)₂— | —O— | 3-trifluoromethylphenyl- |
| 2 | H—C | H—C | H—C | CH₃ | CH₃ | H | —(CH₂)₂— | —S— | benzothiazol-2-yl- |
| 3 | H—C | H—C | H—C | CH₃ | CH₃ | H | —(CH₂)₂— | —O— | 2,4-dichlorophenyl- |
| 4 | H—C | H—C | H—C | CH₃ | CH₃ | H | —(CH₂)₂— | —S— | 4-chlorophenyl- |
| 5 | H—C | H—C | H—C | CH₃ | CH₃ | H | —(CH₂)₂— | —O— | 4-chlorophenyl- |
| 6 | H—C | H—C | H—C | CH₃ | CH₃ | H | —(CH₂)₂— | —O— | 4-phenoxyphenyl- |
| 7 | H—C | H—C | H—C | CH₃ | CH₃ | H | —(CH₂)₂— | —O— | [2,4-dichlorophenyl]—O—(CH₂)₂— |
| 8 | H—C | H—C | H—C | CH₃ | CH₃ | H | —(CH₂)₂— | —O— | 2,4-dichlorophenyl- |
| 9 | H—C | H—C | H—C | CH₃ | CH₃ | H | —(CH₂)₂— | —O— | 3-chlorophenyl- |
| 10 | H—C | H—C | H—C | CH₃ | CH₃ | H | —(CH₂)₂— | —O— | 2-naphtyl- |
| 11 | H—C | H—C | H—C | CH₃ | CH₃ | H | —(CH₃)₂— | —O— | 3-phenoxyphenyl- |
| 12 | H—C | H—C | H—C | CH₃ | CH₃ | H | —(CH₂)₂— | —O— | 5-trifluoromethylpyridin-2-yl- |
| 13 | H—C | H—C | H—C | CH₃ | CH₃ | H | —(CH₂)₂— | —O— | 2,4,6-trichlorophenyl- |
| Rif. 1 | H—C | H—C | H—C | CH₃ | CH₃ | H | —CH₂— | — | H |
| Rif. 3 | H—C | H—C | H—C | CH₃ | CH₃ | H | —CH₂— | — | ethenyl |
| Rif. 5 | H—C | H—C | H—C | CH₃ | CH₃ | H | —CH₂— | — | phenyl |
| Rif. 9 | H—C | H—C | H—C | CH₃ | CH₃ | CH₃ | —CH₂— | — | H |

Rif. 1, 3, 5, 9 are compounds of EP 273572

TABLE 2

| Compound | NMR 200 MHz (CDCCl₃) spectroscopic data |
|---|---|
| 1 | 3,69(3H)s, 3,81(3H)s, 4,25(2H)t, 4,39(2H)t, 6,29(1H)t, 6,58(1H)m, 6,68(1H)m, 7,10–7,42(4H)m, 7,51(1H)s, 7,93(1H)s |
| 2 | 3,65(2H)t, 3,71(3H)s, 3,85(3H)s, 4,38(2H)t, 6,28(1H)t, 6,56(1H)m, 6,67(1H)t, 7,28–7,88(4H)m, 7,52(1H)s, 7,90(1H)s |
| 3 | 3,67(3H)s, 3,83(3H)s, 4,21–4,39(4H)m, 6,27(1H)t, 6,55(1H)m, 6,66(1H)t, 6,89(1H)d, 7,15(1H)dd, 7,34 (1H)d, 7,48(1H)s, 7,89(1H)s |
| 4 | 3,19(2H)t, 3,71(3H)s, 3,86(3H)s, 4,18(2H)t, 6,28(1H) m, 6,55(1H)m, 6,68(1H)m, 7,23–7,34(4H)m, 7,51(1H)s, 7,83(1h)s |
| 5 | 3,55(3H)s, 3,75(3H)s, 4,15(4H)m, 6,00–7,28(7H)m, 7,40(1H)s, 3,85(1H)s |
| 6 | 3,69(3H)s, 3,83(3H)s, 4,19(2H)t, 4,37(2H)t, 6,28(1H) m, 6,57(1H)m, 6,89–7,33(9H)m, 7,51(1H)s, 7,93(1H)s |
| 7 | 3,70(3H)s, 3,80–3,91(7H)m, 4,13–4,22(4H)m, 6,27(1H)m 6,55(1H)m, 6,65(1H)m, 6,86(1H)d, 7,14(1H)dd, 7,34 (1H)d, 7,59(1h)s, 7,89(1H)s |
| 8 | 1,77–2,00(4H)m, 3,70(3H)s, 3,84(3H)s, 4,02(2H)t, 4,10 (2H)t, 6,27(1H)m, 6,55(1H)m, 6,65(1H)m, 6,83(1H)d 7,15(1H)dd, 7,34(1H)d, 7,51(1H)s, 7,85(1H)s |
| 9 | 7.90(1H, s), 7.50(1H, s), 6.86(3H, m), 6.66(1H, q), 6.56(1H, q), 6.27(1H, q), 4.34(2H, t), 4.18(2H, t), 3.82(3H, s), 3.68(3H, s). |

TABLE 3

| Product | Dosages (ppm) | Peronospora vite preventive 1 g | Helminhosporium Teres preventive 1 g |
|---|---|---|---|
| 1 | 500 | 100 | 100 |
|  | 125 | 100 | 100 |
|  | 30 | 90 | 100 |
|  | 7.5 | 54 | 90 |
| 2 | 500 | 100 | 100 |
|  | 125 | 100 | 90 |
|  | 30 | 100 | 80 |
|  | 7.5 | 94 | 60 |
| 4 | 500 | 100 | 100 |
|  | 125 | 100 | 100 |
|  | 30 | 95 | 100 |
|  | 7.5 | 70 | 80 |
| 5 | 500 | 100 | 100 |
|  | 125 | 100 | 100 |
|  | 30 | 100 | 90 |
|  | 7.5 | 90 | 70 |
| Rif. 1 | 500 | 50 | 30 |
|  | 125 | 0 | 0 |
|  | 30 | 0 | 0 |
|  | 7.5 | 0 | 0 |
| Rif. 3 | 500 | 100 | 60 |
|  | 125 | 100 | 30 |
|  | 30 | 80 | 15 |
|  | 7.5 | 30 | 0 |
| Rif. 5 | 500 | 100 | 26 |
|  | 125 | 93 | 0 |
|  | 30 | 67 | 0 |

TABLE 3-continued

| Product | Dosages (ppm) | *Peronospora vite* preventive 1 g | *Helminhosporium Teres* preventive 1 g |
|---|---|---|---|
|  | 7.5 | 15 | 0 |
| Rif. 9 | 500 | 32 | — |
|  | 125 | 10 | 80 |
|  | 30 | 0 | 45 |
|  | 7.5 | 0 | 30 |

We claim:

1. Oximic derivatives with a fungicide activity having the formula:

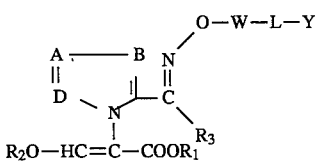

wherein:

A, B, D, the same or different, represent a nitrogen atom, or a =C—G group;

G represents a hydrogen atom, a halogen atom, the nitro group, the cyano group, a —$COOR_4$ group, a $C_1$-$C_6$ alkyl group or $C_1$-$C_6$ haloalkyl group;

$R_1$, $R_2$, $R_4$ and $R_5$, the same or different, represent $C_1$-$C_6$ alkyl or $C_1$-$C_6$ haloalkyl groups;

$R_3$ represents a hydrogen atom, a $C_1$-$C_6$ alkyl group or $C_1$-$C_6$ haloalkyl group, or a —$COOR_5$ group;

W represents a linear or branched $C_2$-$C_{10}$ alkylene group, possibly substituted with one or more halogen atoms, or a $C_3$-$C_6$ cycloalkyl, a $C_4$-$C_8$ cycloalkylalkyl;

L represents O or S;

Y represents a phenyl, a naphthyl, a heterocycle with 5–6 atoms wherein the hetero-atoms are O, N, S, a benzo-condensated heterocycle with 9–10 atoms wherein the hetero-atoms are selected from oxygen, nitrogen, sulphur, all said groups optionally substituted with one or more groups selected from: halogen atoms, $C_1$-$C_4$ alkyls or $C_1$-$C_4$ haloalkyls, $C_1$-$C_4$ alkoxyls or $C_1$-$C_4$ haloalkoxyls, phenyl groups or phenoxylic groups suitably substituted;

Y can also be a linear or branched alkyl substituted with one or more groups selected from: halogen atoms, $C_1$-$C_4$ alkoxyls or $C_1$-$C_4$ haloalkoxyls or $C_1$-$C_4$ haloalkoxyhaloalkoxyl, phenyl or phenoxylic groups.

2. Oximic derivatives according to claim 1, wherein:

A, B, D represent =C—G, where G is a hydrogen atom;

$R_1$, $R_2$ are $CH_3$;

$R_3$ is hydrogen

W is $C_2$-$C_4$ alkylene;

L is O or S;

Y is a $C_1$-$C_4$ haloalkylphenyl, phenyl substituted with halogen and/or with $C_1$-$C_4$ alkoxy, or benzothiazolyl.

3. Compound according to claim 1 which is (Z)-3-methoxy-2-{2-[2-(3-trifluoromethylphenoxy)ethoxyiminometbyl] pyrrol-1-1}-methyl prop-2-enoate.

4. Compound according to claim 1 wherein: W is —$(CH_2)_2$—, L is S, Y is 2-benzothiazolyl.

5. Compound according to claim 1 wherein: W is —$(CH_2)_2$—, L is O, Y is 2,4-dichlorophenyl.

6. Compound according to claim 1 wherein: W is —$(CH_2)_2$—, L is S, Y is 4-chlorophenyl.

7. Compound according to claim 1 wherein: W is —$(CH_2)_2$—, L is O, Y is 4-chlorophenyl.

8. Compound according to claim 1 wherein: W is —$(CH_2)_2$—, L is O, Y is 4-phenoxyphenyl.

9. Compound according to claim 1 wherein: W is —$(CH_2)_2$—, L is O, Y is —$(CH_2)_2$—O—2,4-dichlorophenyl.

10. Compound according to claim 1 wherein: W is —$(CH_2)_4$—, L is O, Y is 2,4-dichlorophenyl.

11. Fungicidal compositions containing one or more of the compounds according to claim 1 either alone or together with solid supports, liquid diluents, surface-active agents, or other active principles.

12. Method for fighting fungal infections consisting in spraying the plants with one or more compounds according to claim 1 either alone or in the presence of solid supports, liquid diluents, surface-active agents, or other active principles.

* * * * *